(12) United States Patent
Gallagher et al.

(10) Patent No.: US 10,980,634 B2
(45) Date of Patent: Apr. 20, 2021

(54) MEDICAL DEVICE DELIVERY SYSTEM AND METHODS OF DELIVERING MEDICAL DEVICES

(71) Applicant: Medtronic CV Luxembourg S.a.r.l., Luxembourg (LU)

(72) Inventors: John Gallagher, Galway (IE); Niall Duffy, Galway (IE); Declan Costello, Galway (IE); Oisin Cooney, Galway (IE)

(73) Assignee: MEDTRONIC CV LUXEMBOURG S.A.R.L., Luxembourg (LU)

( * ) Notice: Subject to any disclaimer, the term of this patent is extended or adjusted under 35 U.S.C. 154(b) by 216 days.

(21) Appl. No.: 16/040,242

(22) Filed: Jul. 19, 2018

(65) Prior Publication Data

US 2018/0325667 A1   Nov. 15, 2018

Related U.S. Application Data

(62) Division of application No. 13/673,609, filed on Nov. 9, 2012, now abandoned.

(51) Int. Cl.
| | |
|---|---|
| *A61F 2/24* | (2006.01) |
| *A61F 2/95* | (2013.01) |
| *A61F 2/966* | (2013.01) |
| *A61F 2/958* | (2013.01) |

(52) U.S. Cl.
CPC .......... *A61F 2/2427* (2013.01); *A61F 2/2433* (2013.01); *A61F 2/2436* (2013.01); *A61F 2/95* (2013.01); *A61F 2/2418* (2013.01); *A61F 2002/9505* (2013.01); *A61F 2002/9534* (2013.01); *A61F 2002/9583* (2013.01); *A61F 2002/9665* (2013.01);

(Continued)

(58) Field of Classification Search
CPC .......... A61F 2/011; A61F 2/2427–2439; A61F 2002/9505; A61F 2002/9511; A61B 2017/1205; A61B 2017/12054
See application file for complete search history.

(56) References Cited

U.S. PATENT DOCUMENTS

| | | | |
|---|---|---|---|
| 5,601,600 A | * | 2/1997 | Ton .................. A61B 17/12022 606/191 |
| 5,733,325 A | | 3/1998 | Robinson et al. |
| 6,267,783 B1 | | 7/2001 | Letendre et al. |

(Continued)

FOREIGN PATENT DOCUMENTS

| | | |
|---|---|---|
| EP | 2111828 B1 | 2/2012 |
| WO | 2012/032187 A1 | 3/2012 |
| WO | 2013/154678 A1 | 10/2013 |

OTHER PUBLICATIONS

The International Search Report and Written Opinion issued in International Application No. PCT/US2013/068343, dated Jun. 18, 2014.

*Primary Examiner* — Katherine M Shi
*Assistant Examiner* — Lindsey Bachman

(57) ABSTRACT

In some embodiments, a medical device delivery system includes a catheter and a retainer. The retainer can be engaged with the medical device to restrain relative movement of the medical device in one or more axial and/or radial directions. A variety of retainers and retainer systems are disclosed, many of which can reliably disengage the medical device from the retainer. Methods for using the medical device delivery system are also described.

10 Claims, 16 Drawing Sheets

(52) U.S. Cl.
CPC ............. *A61F 2230/0095* (2013.01); *A61F 2230/0097* (2013.01); *A61F 2250/0003* (2013.01)

(56) References Cited

U.S. PATENT DOCUMENTS

| | | |
|---|---|---|
| 6,673,106 B2 | 1/2004 | Mitelberg et al. |
| 6,790,221 B2 | 9/2004 | Monroe et al. |
| 7,445,631 B2 | 11/2008 | Salahieh et al. |
| 7,459,192 B2 | 12/2008 | Parsonage et al. |
| 7,611,528 B2 * | 11/2009 | Goodson, IV .......... A61F 2/962 623/1.11 |
| 8,052,732 B2 | 11/2011 | Mitchell et al. |
| 8,157,852 B2 | 4/2012 | Bloom et al. |
| 8,231,670 B2 | 7/2012 | Salahieh et al. |
| 2004/0220585 A1 | 11/2004 | Nikolchev |
| 2006/0111771 A1 | 5/2006 | Ton et al. |
| 2006/0276872 A1 | 12/2006 | Arbefeuille et al. |
| 2007/0088420 A1 | 4/2007 | Andreas et al. |
| 2007/0250151 A1 | 10/2007 | Pereira |
| 2007/0293928 A1 * | 12/2007 | Tomlin ............. A61B 17/12022 623/1.11 |
| 2009/0270967 A1 | 10/2009 | Fleming, III et al. |
| 2009/0287290 A1 | 11/2009 | Macaulay et al. |
| 2010/0049313 A1 | 2/2010 | Alon et al. |
| 2011/0098805 A1 | 4/2011 | Dwork et al. |
| 2011/0251675 A1 | 10/2011 | Dwork |
| 2011/0257720 A1 | 10/2011 | Peterson et al. |
| 2011/0264203 A1 | 10/2011 | Dwork et al. |
| 2013/0131775 A1 | 5/2013 | Hadley et al. |
| 2014/0018915 A1 | 1/2014 | Biadillah et al. |

* cited by examiner

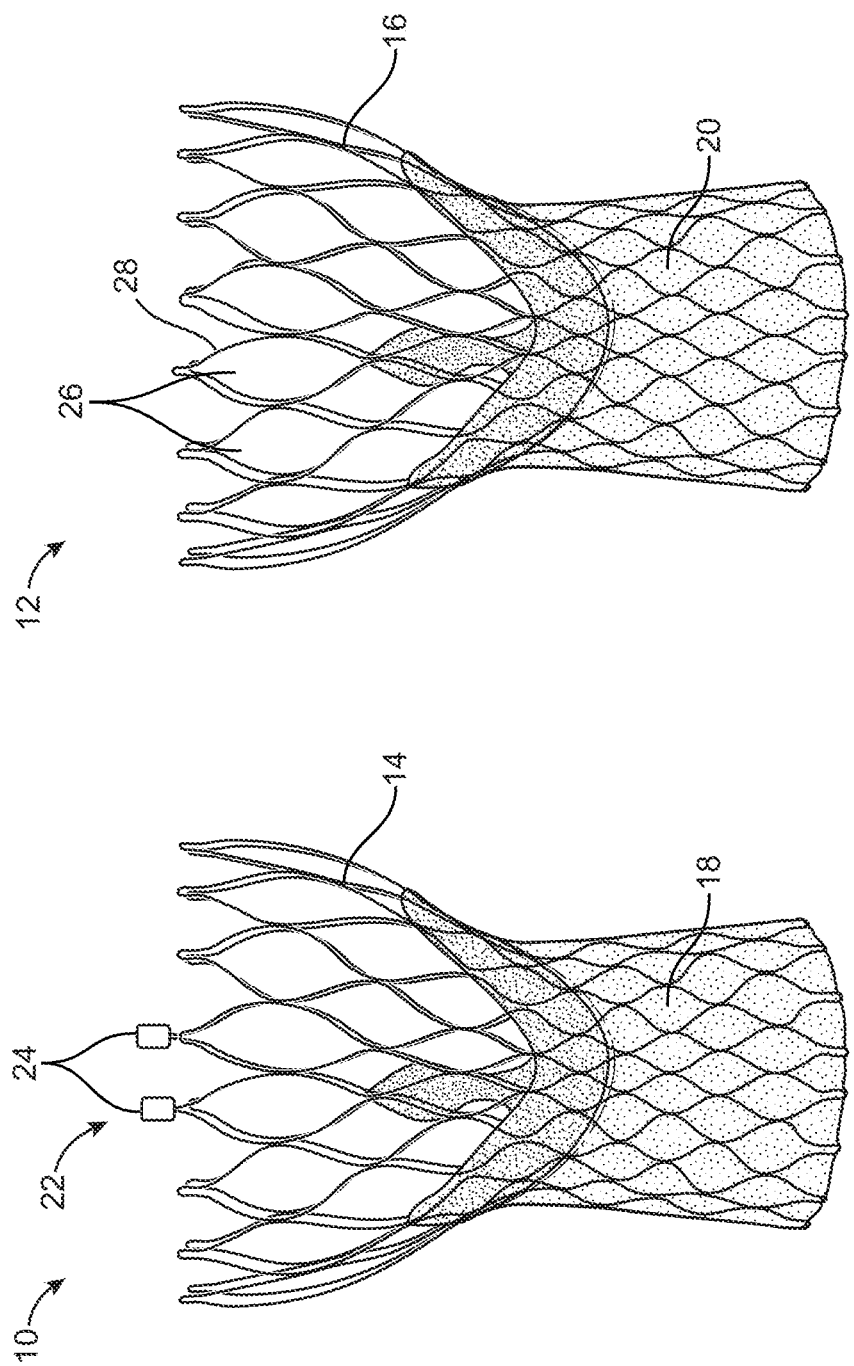

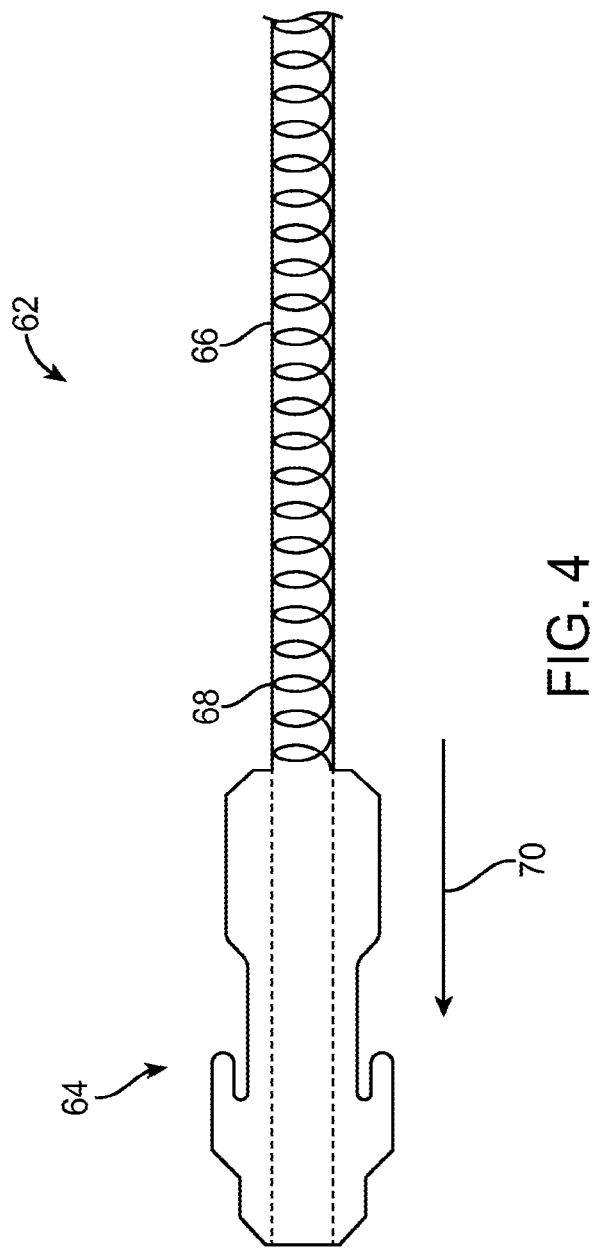

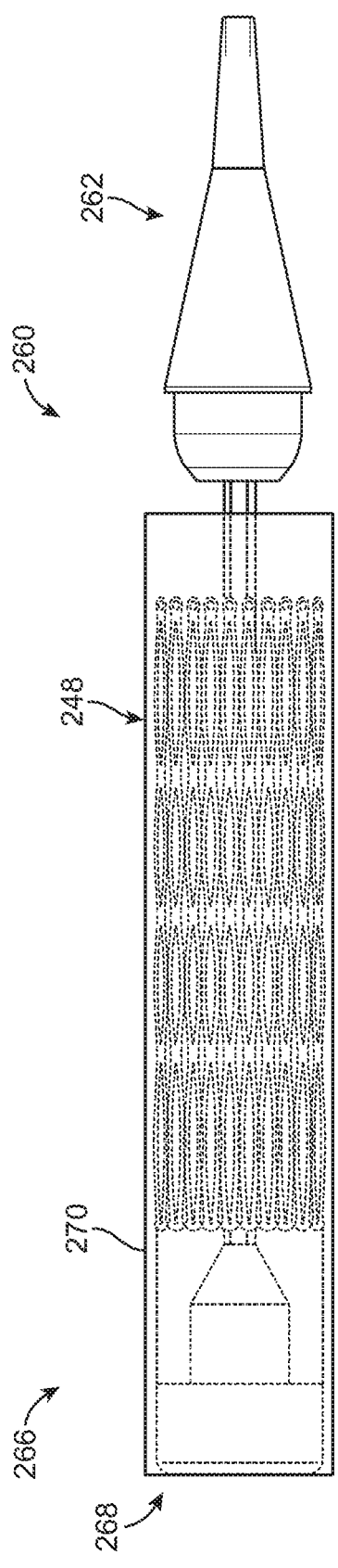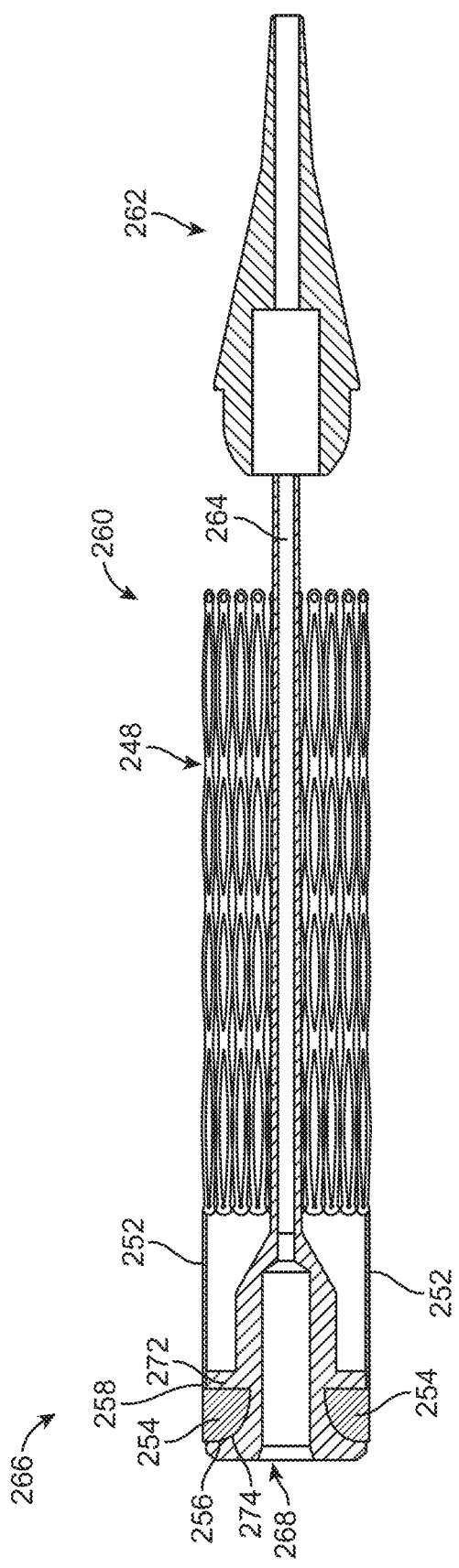

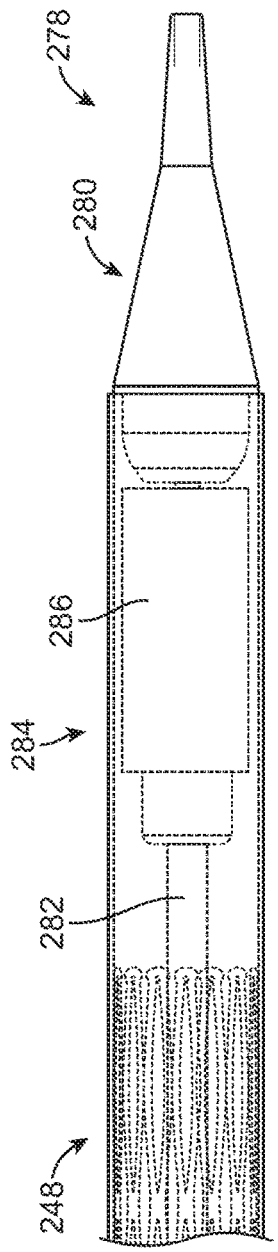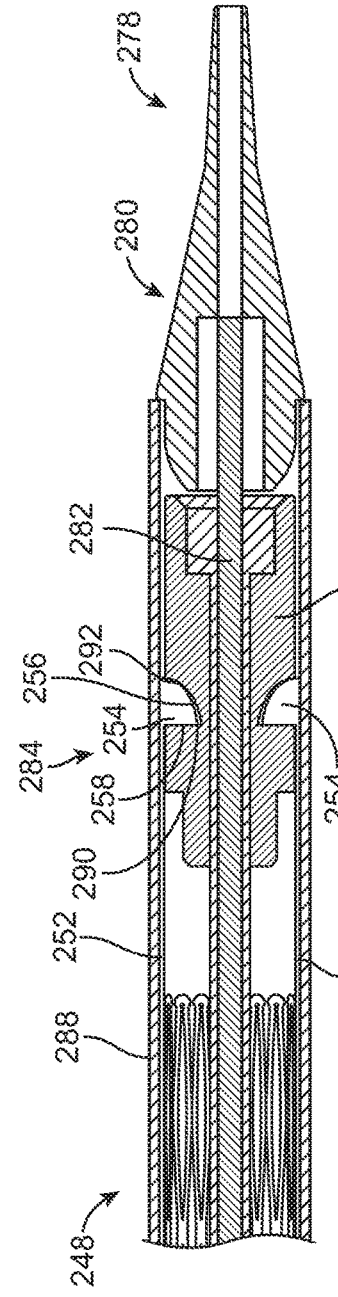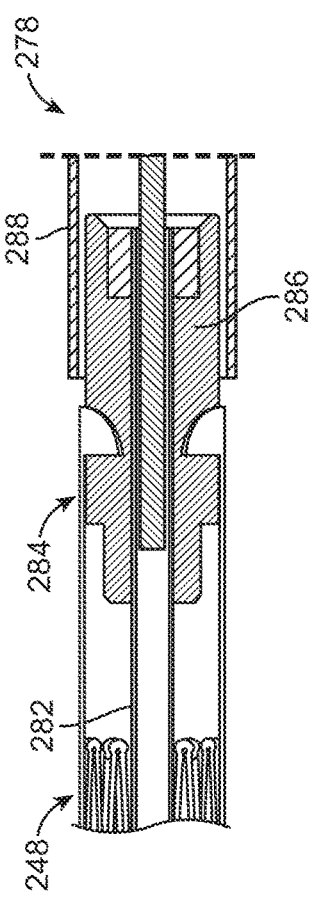

MEDICAL DEVICE DELIVERY SYSTEM AND METHODS OF DELIVERING MEDICAL DEVICES

CROSS-REFERENCE TO RELATED APPLICATIONS

This application is a divisional of U.S. application Ser. No. 13/673,609, filed Nov. 9, 2012, the contents of which are incorporated by reference herein in their entirety.

BACKGROUND

Field

Certain embodiments of the present invention are related to medical device delivery systems and methods of delivering medical devices.

Background Art

Medical devices can be delivered to a site within a patient through a variety of techniques. For example, a medical device can be implanted or otherwise delivered through conventional open surgical techniques, such as for example open-heart surgery. In some embodiments, the medical device can be implanted or delivered percutaneously. For example, in some percutaneous techniques, a medical device, such as a valve prosthesis can be compacted and loaded onto a delivery device for advancement through a patient's vasculature in a transfemoral, transapical, or transatrial procedure. There is a continuous need for improved delivery systems for use in such surgical, percutaneous, and other delivery techniques.

BRIEF SUMMARY

In some embodiments, a medical device delivery system includes a catheter and a retainer disposed within the catheter and engaged with the medical device to restrain relative movement of the medical device in a first axial direction. The retainer can include a curved surface configured to disengage the medical device from the retainer when there is a predetermined amount of relative movement between the medical device and the retainer in a second axial direction.

In some embodiments, a medical device delivery system includes a catheter, a retainer disposed within the catheter and engaged with the medical device to restrain relative movement of the medical device in an axial direction, and an inflatable balloon configured to facilitate disengagement of the medical device from the retainer by providing a radially outward force on a portion of the medical device when the balloon is inflated.

In some embodiments, a medical device delivery system includes a catheter having a lumen, a shaft having a lumen and disposed within the catheter lumen, and a retainer disposed within the shaft lumen and engaged with the medical device to restrain relative movement of the medical device in an axial direction. The shaft can include a protrusion extending from an inside surface of the shaft lumen that is configured to disengage the medical device from the retainer when the retainer engages the protrusion.

In some embodiments, a medical device delivery system includes a catheter, a retainer disposed within the catheter and engaged with the medical device to restrain relative movement of the medical device in an axial direction, and an actuator configured to radially retract the retainer and disengage the medical device from the retainer.

In some embodiments, a medical device delivery system includes a catheter, a base disposed within a lumen of the catheter and engaged with the medical device to restrain relative movement of the medical device in an axial direction, and a sheath covering the base and engaged with a portion of the medical device to restrain relative movement of the medical device in a radial direction.

In some embodiments, a medical device delivery system includes a catheter, a base disposed within a lumen of the catheter and engaged with the medical device to restrain relative movement of the medical device in an axial direction, and a pin disposed within the base and engaged with the medical device to restrain relative movement of the medical device in a radial direction. The pin can retract to disengage the medical device from the base.

In some embodiments, a medical device delivery system includes a catheter, a first retainer disposed within the catheter and engaged with the medical device to restrain relative movement of the medical device in an axial direction, and a second retainer disposed within the catheter and engaged with the medical device to restrain relative movement of the medical device in an outward radial direction. The second retainer is configured such that relative movement in an axial direction between the second retainer and the medical device allows the medical device to disengage from the retainer.

In some embodiments, a medical device delivery system includes a catheter and a retainer configured to restrain a medical device in an axial direction. The medical device can include a coupling portion configured to engage with the retainer. The coupling portion can have a curved surface that facilitates disengagement of the medical device from the retainer.

BRIEF DESCRIPTION OF THE DRAWINGS/FIGURES

The accompanying figures, which are incorporated herein, form part of the specification and illustrate embodiments of a valve prosthesis frame and delivery system. Together with the description, the figures further serve to explain the principles of and to enable a person skilled in the relevant art(s) to make, use, and implant the valve prosthesis described herein.

FIG. 1A illustrates a front view of a medical device for use with one or more of the medical device delivery systems described herein.

FIG. 1B illustrates a front view of a medical device for use with one or more of the medical device delivery systems described herein.

FIG. 4 is an illustration of a portion of a retainer system in accordance with an embodiment.

FIG. 15A illustrates a front view of a delivery catheter in accordance with an embodiment.

FIG. 15B illustrates a cross-sectional view of the delivery catheter of FIG. 15B.

FIG. 16A illustrates a front view of a delivery catheter in accordance with an embodiment.

FIG. 16B illustrates a cross-sectional view of the delivery catheter of FIG. 16A at a first stage in a delivery operation.

FIG. 16C illustrates a cross-sectional view of a portion of the delivery catheter of FIG. 16A at a second stage in a delivery operation.

DETAILED DESCRIPTION

Figure 2B:
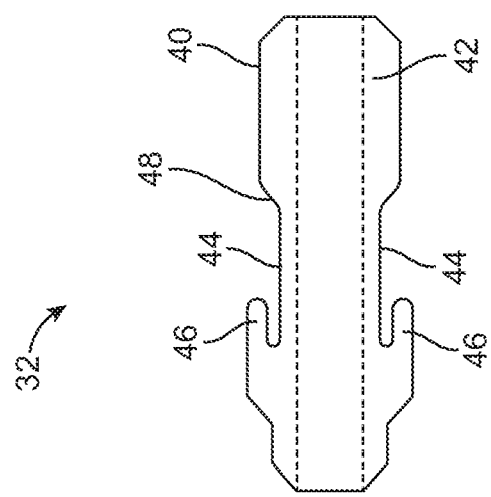
FIG. 2B illustrates a cross-sectional view of a retainer of the delivery catheter of FIG. 2A.

The following detailed description refers to the accompanying figures which illustrate several embodiments. Other embodiments are possible. Modifications can be made to the embodiments described herein without departing from the spirit and scope of the present invention. Therefore, the following detailed description is not meant to be limiting.

FIG. 1A-1B illustrate front views of medical devices 10 and 12. Medical devices 10 and 12 are shown in the form of prosthetic heart valves including frames 14 and 16 with valve bodies 18 and 20 attached thereto. Medical device 10 includes coupling portions 22 in the form of eyelets 24. Other suitable types of coupling portions, such as those shown for example in FIG. 13 can be used. Coupling portions 22 can extend from frame 14 or can be attached or otherwise connected to frame 14. Coupling portions 22 can be formed and/or reinforced for engagement with one or more of the retainer systems, retainers, or delivery catheters described herein. Coupling portions 22 are shown disposed on a distal end of frame 14. As used herein, the terms "distal" or "outflow" are understood to mean downstream to the direction of blood flow. The terms "proximal" or "inflow" are understood to mean upstream to the direction of blood flow. In some embodiments, coupling portions 22 can be disposed on a proximal end of frame 14, in a longitudinal center of frame 14, or in any other desired location on or in a medical device, such as medical device 10. In some embodiments, coupling portions 22 can be located on both a distal end and a proximal end of medical device 10. In some embodiments, coupling portions 22 can extend from a coupling piece attached to frame 14. In some embodiments, the medical device does not include eyelets 24. One embodiment of such a medical device is shown for example in FIG. 1B. Medical device 12 includes openings 26, formed by one or more wires 28 of frame 16 which can serve as coupling portions. For example, in some embodiments, one or more of the retainer systems can be attached directly or indirectly to openings 26 instead of eyelets.

Suitable medical devices are not limited to prosthetic heart valves. For example, in some embodiments, the medical device can be a device configured to be transported via a delivery catheter. In some embodiments, the medical device can be an expandable device, such as, for example, a percutaneously delivered device configured to be compacted and loaded onto a delivery catheter for advancement through a patient's vasculature. The device can also be a non-implantable device. For example, in some embodiments, the device can be an embolic filter that is not designed to be implanted within the patient's body. In some embodiments, the device can be a tool that can be used, for example, to retrieve an item from inside a patient.

Figure 2A:
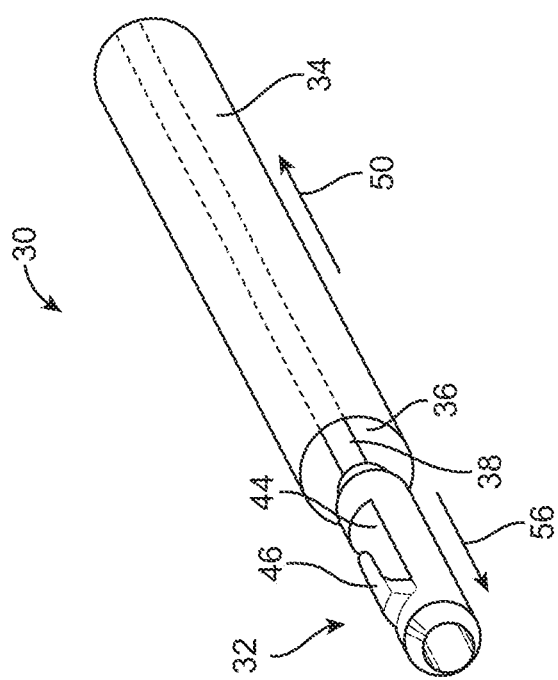
FIG. 2A illustrates a front-perspective view of a portion of a delivery catheter in accordance with an embodiment.

FIGS. 2A-2B respectively illustrate a front perspective view of a portion of a delivery catheter 30 including a retainer 32 and a cross-sectional view of retainer 32 in accordance with an embodiment. Delivery catheter 30 can include a sheath 34, with retainer 32 disposed within a lumen 36 of sheath 34, and a shaft 38 connected to retainer 32. In some embodiments, retainer 32 can be configured to both retain and controllably release a medical device. Retainer 32 can have a body 40 including a lumen 42 configured to receive shaft 38. Retainer 32 can have a recessed portion 44 extending around an entire perimeter of retainer 32 or only a portion thereof. In some embodiments, body 40 can be substantially cylindrical or any other suitable shape.

Retainer 32 can include one or more extensions 46 extending over recessed portion 44. In some embodiments, extensions 46 can be in the form of a hook. For example, two extensions 46 can be disposed about 180 degrees apart along the radial periphery of retainer 32. In some embodiments, retainer 32 includes only a single extension 46. In some embodiments, retainer 32 includes more than two extensions that are uniformly or nonuniformly disposed along the radial periphery of retainer 32. In some embodiments, separate recessed portions 44 are formed for each extension 46 of retainer 32.

The configuration of recessed portion 44 and extensions 46 can allow retainer 32 to secure a portion of a medical device between recessed portion 44 and extensions 46 to restrain radially outward movement thereof. In some embodiments, retainer 32 includes a curved surface 48 that can be configured to force at least a portion of the medical device to radially expand and disengage from the retainer when the medical device is moved in an axial direction against curved surface 48. In some embodiments, retainer 32 is configured to restrain movement of the medical device in single axial direction, such as for example axial direction 50. To facilitate movement of retainer 32 in one or both axial directions, retainer 32 can be spring-loaded. One embodiment of such a configuration is illustrated in FIG. 4 and described further herein.

In some embodiments, one or more of the retainers or retainer systems described herein, such as retainer 32, can retain and controllably release the medical device without requiring modification to the medical device. For example, extensions 46 can be configured to attach to the medical device itself without requiring distinct coupling portions, such as eyelets. In embodiments in which the medical device is a valve prosthesis frame having a mesh or lattice framework, extensions 46 can be configured to extend directly into the frame via openings in the frame, such as openings 26 of frame 16 shown and described with respect to FIG. 1B.

One example of a delivery operation for delivery catheter 30 is described below. For this and other methods described herein, it should be noted that not every act need be performed and additional acts can be included as would be apparent to one of ordinary skill in the art. In addition, the acts can be reordered as desired. Other medical devices and delivery techniques can be used with any of the retainers, retainer systems, or delivery catheters described herein.

A valve prosthesis including a frame with eyelets is first compressed for delivery via delivery catheter 30. Retainer 32 is connected to the eyelets via extensions 46. Retainer 32 is pulled into delivery catheter 30 along with the medical device. In some embodiments, delivery catheter 30 can be advanced in a retrograde manner through the patient's femoral artery and into the patient's descending aorta. It is understood that the femoral approach is only exemplary and that other delivery routes, such as a radial approach or another approach, can be employed.

Figure 3:
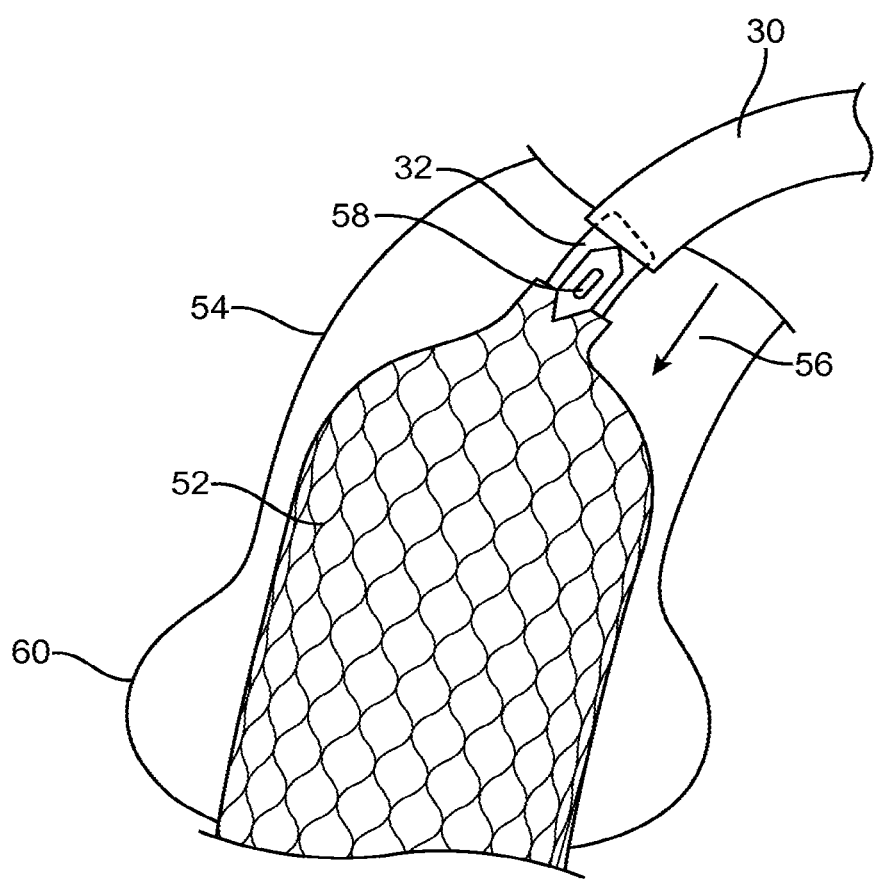
FIG. 3 illustrates a stage of a delivery operation of the delivery catheter of FIG. 2A.

The valve prosthesis is then deployed within a body lumen of the patient's aortic valve. FIG. 3 illustrates an example of an expanded valve prosthesis 52 within a body lumen 54 of a patient. Retainer 32 can release valve prosthesis 52 by moving in axial direction 56 relative to the frame in a range from about 1 mm to about 2 mm. This can force a portion of the valve prosthesis against curved surface 48 of retainer 32 to release eyelets 58 of valve prosthesis 52 from retainer 32. Valve prosthesis 52 is then free to expand against body lumen 54. In some embodiments, valve prosthesis 52 can expand against an annulus 60 within body lumen 54.

In some embodiments, retainer 32 is disengaged from valve prosthesis 52 after valve prosthesis 52 expands against annulus 60. Once valve prosthesis 52 is disengaged from retainer 32, retainer 32 can be pulled back into delivery catheter 30. One or more features of retainer 32, delivery catheter 30, and/or the delivery methods described above can be used or adapted for use with any of the other retainers, retainer systems, and/or delivery catheters described herein.

FIG. 4 is an illustration of retainer system 62 in accordance with an embodiment. Retainer system 62 includes retainer 64 attached to a shaft 66. A spring 68 can be disposed around or within shaft 66. Like several other retainer systems described herein, retainer system 62 can be configured to both retain and controllably release a medical device. For example, retainer system 62 can release a medical device by movement of retainer 64 in axial distal direction 70. To facilitate movement of retainer 64 in direction 70, retainer system 62 can use spring 68 to spring-load retainer 64. In some embodiments, a spring-loaded retainer system can be configured to facilitate movement of retainer 64 in any desired direction. One or more features of retainer 64, retainer system 62, and/or spring 68 can be used or adapted for use with any of the other retainers, retainer systems, and/or delivery catheters described herein.

Figure 5B:
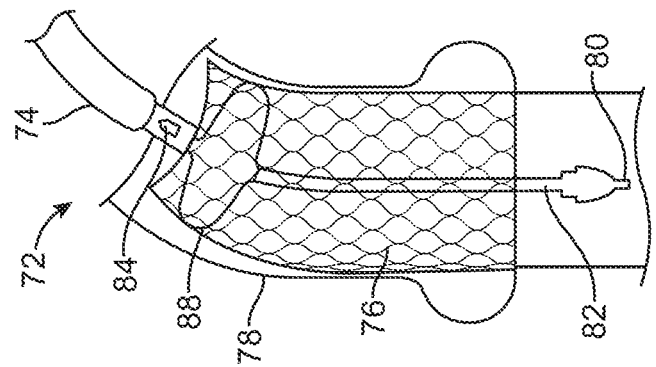
FIG. 5B illustrates a view of the retainer system of FIG. 5A at a second stage in a delivery operation.
Figure 5A:
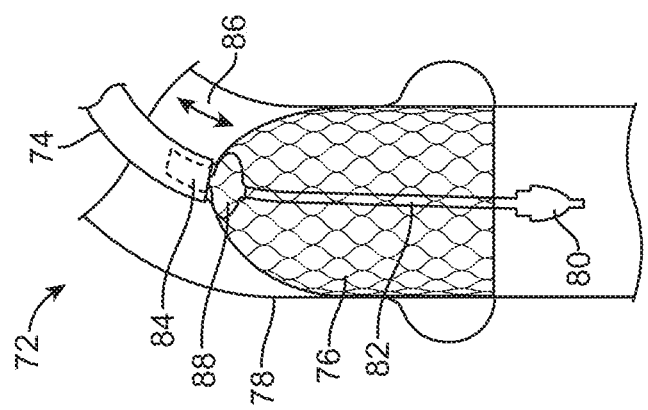
FIG. 5A illustrates a view of a retainer system in accordance with an embodiment at a first stage in a delivery operation.

FIGS. 5A and 5B illustrate views of a retainer system 72 in accordance with an embodiment. FIG. 5A illustrates retainer system 72 and delivery catheter 74 connected to a medical device 76 within a body lumen 78 of a patient. Delivery catheter 74 can include a tip 80 attached to a shaft 82. Like several of the retainer systems described herein, retainer system 72 can be configured to both retain and controllably release a medical device. For example, retainer system 72 can include a retainer 84 that can be configured to restrain medical device 76 in one or both axial directions 86.

Retainer system 72 can include an inflatable balloon 88 disposed immediately distal to retainer 84 and within a portion of medical device 76. Balloon 88 can be configured to force at least a portion of medical device 76 to radially expand and disengage from retainer 84 when balloon 88 is inflated. For example, FIG. 5B illustrates a view of retainer system 72 after balloon 88 has been inflated. In some embodiments, balloon 88 need only be partially inflated. In some embodiments, balloon 88 must be fully inflated. In some embodiments, balloon 88 is configured to contact a wall of body lumen 78 when balloon 88 is expanded. In some embodiments, balloon 88 is substantially the same size as retainer 84 when inflated. One or more features of retainer 84, retainer system 72, balloon 88, and/or delivery catheter 74 can be used or adapted for use with any of the other retainers, retainer systems, and/or delivery catheters described herein.

Figure 6A:
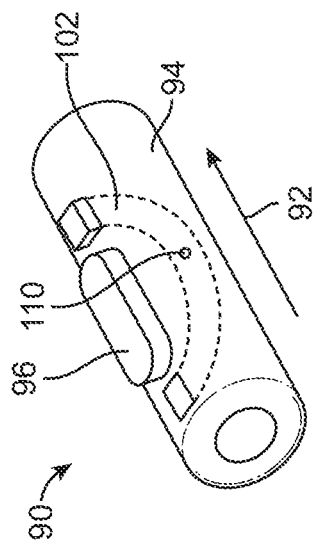
FIG. 6A illustrates a front-perspective view of a retainer in accordance with an embodiment at a first stage in a delivery operation.
Figure 6C:
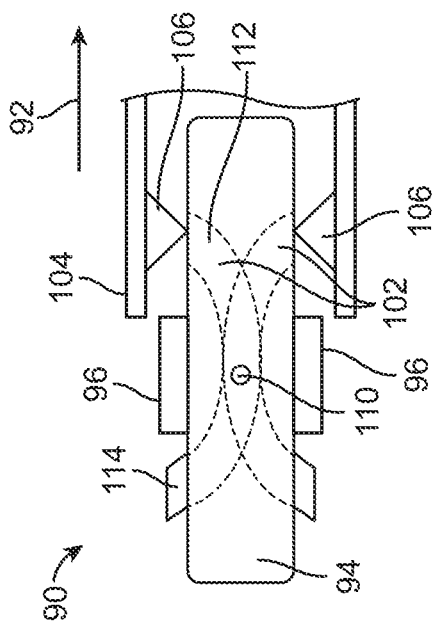
FIG. 6C illustrates a front view of the retainer of FIG. 6A at a second stage in a delivery operation.
Figure 6B:
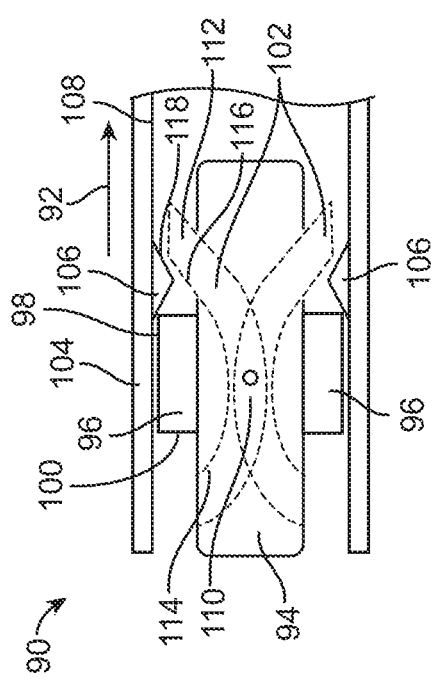
FIG. 6B illustrates a front view of the retainer of FIG. 6A at a first stage in a delivery operation.

FIGS. 6A-C illustrate retainer 90 in accordance with an embodiment. FIG. 6A shows a front-perspective view of retainer 90. FIG. 6B shows a partially cross-sectional view of retainer 90 in a first state. FIG. 6C shows a partially cross-sectional view of retainer 90 in a second state. Like several of the retainers described herein, retainer 90 can be configured to both retain and controllably release a medical device. For example, retainer 90 can release a medical device by moving in one or both axial directions, such as axial direction 92.

Retainer 90 includes a base 94 having one or more protrusions 96 configured to restrain a corresponding portion of a medical device. Stepped surfaces 98 and 100 of protrusion 96 are configured to engage with a coupling portion of the medical device, such as eyelets (not shown), in order to restrain movement of the medical device in one or both axial directions.

Retainer 90 includes one or more actuators 102 configured to engage with a shaft 104 via corresponding protrusion 106 formed on an inside surface 108 thereof.

In some embodiments, actuators 102 can be in the form of toggles that bump a medical device off retainer 90. In some embodiments, one or more actuators 102 include a hinge 110 which can allow actuator 102 to rotate relative to hinge 110 so that when a first end 112 of actuator 102 extending outward from base 94 is retracted inward, a second end 114 of actuator 102 is moved outward. In some embodiments, actuator 102 includes an angled surface 116 configured to engage with a corresponding angled surface 118 of protrusion 106 within shaft 104. One or both of angled surfaces 116 and 118 can be configured to translate axial movement of first end 112 into radial movement, which can allow actuator 102 to rotate around hinge 110. When second end 114 moves outward it can push a portion of a medical device, such as eyelets off of protrusions 106. FIGS. 6A and 6B show actuator 102 before it is rotated, with first end 112 extending outward from base 94, whereas FIG. 6C shows actuator 102 after it is rotated, with second end 114 extending outward from base 94. Actuator 102 can have any suitable shape. For example, as shown in FIGS. 6A-C, retainer 90 can include two substantially U-shaped actuators 102 which rotate independently from each other. One or more features of retainer 90 can be used or adapted for use with any of the other retainers, retainer systems, and/or delivery catheters described herein.

Figure 7A:
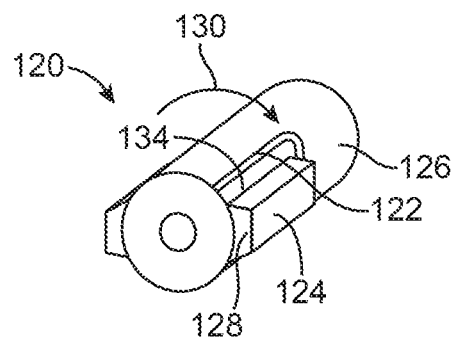
FIG. 7A illustrates a front-perspective view of a retainer in accordance with an embodiment at a first stage in a delivery operation.
Figure 7B:
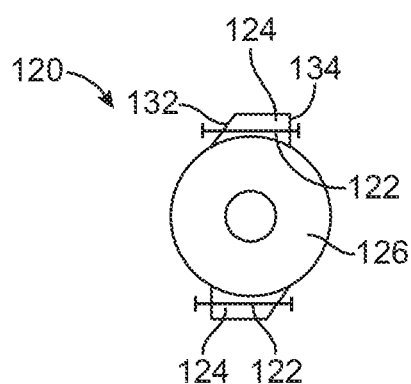
FIG. 7B illustrates a side view of the retainer of FIG. 7A at a first stage in a delivery operation.
Figure 7C:
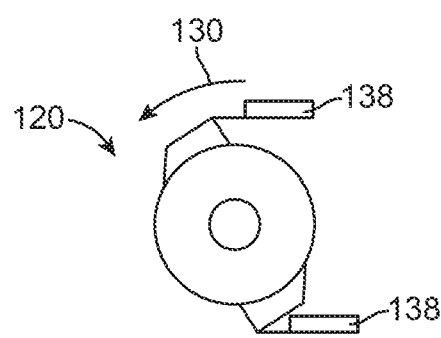
FIG. 7C illustrates a side view of the retainer of FIG. 7A at a second stage in a delivery operation.

FIGS. 7A-C illustrate retainer 120 in accordance with an embodiment. FIGS. 7A and 7B respectively illustrate a front-perspective view and a side view of retainer 120 attached to eyelets 122 of a medical device. FIG. 7C shows a side view of retainer 120 rotated in a counter-clockwise direction relative to FIG. 7B and detached from eyelets 122. Like several of the retainers described herein, retainer 120 can be configured to both retain and controllably release a medical device.

Retainer 120 includes one or more protrusions 124 extending from base 126. Protrusions 124 can be configured to restrain a corresponding portion of a medical device, such as eyelets 122. Stepped surface 128 of protrusion 124 is configured to engage with a coupling portion of the medical device, such as eyelets 122, in order to restrain movement of the medical device in one or both axial directions. Retainer 120 can release eyelets 122 by moving in a rotational direction 130 or other rotational direction. For example, in some embodiments, protrusions 124 can include a surface, such as angled surface 132, which can facilitate removal of the medical device as retainer 120 is rotated. In some embodiments, retainer 120 can include multiple angled or curved surfaces, or a combination thereof. In some embodiments, retainer 120 can include a stepped surface 134 on one side of retainer 120 which does not facilitate release of eyelets 122 when retainer 120 is rotated against stepped surface 134. In some embodiments, both surfaces 132 and 134 of retainer 120 are angled so that rotation of retainer 120 in either direction can facilitate release of eyelets 122.

Figure 7D:
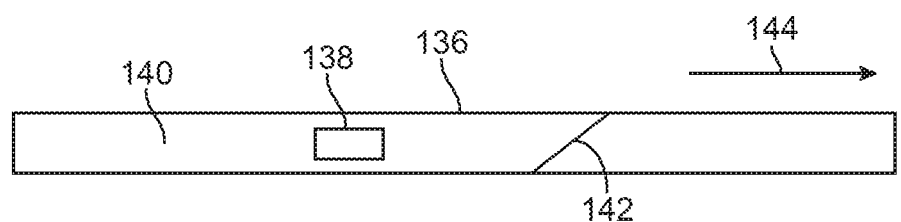
FIG. 7D illustrates a front view of a shaft for use with the retainer of FIG. 7A.

FIG. 7D illustrates a cross-sectional view of a shaft 136 that can be used with retainer 120. Shaft 136 includes one or more protrusions 138 located on an inside surface of a lumen 140 of shaft 136. In some embodiments, one or more protrusions 124 of retainer 120 are configured to engage with one or more protrusions 138 of shaft 136 to facilitate detaching eyelets from retainer 120. In some embodiments, protrusions 124 can be configured to "knock" or "bump" off eyelets 122 as retainer 120 is rotated.

In some embodiments, shaft 136 is configured to be rotated while retainer 120 does not rotate. In some embodiments, as shaft 136 is rotated, protrusions 138 of shaft 136 can "knock" or "bump" off the medical device from protrusions 124 of retainer 120. In some embodiments, shaft 136 can include an angled surface 142 which can translate axial movement of shaft 136 into rotational movement of shaft 136. For example, as shown in FIG. 7D, shaft 136 can include an angled surface 142 on an inside surface of lumen 140, that can engage with a surface (not shown) within the delivery system to force rotation of shaft 136 as shaft 136 is moved in axial direction 144. In some embodiments, angled surface 142 can be located on an outside surface of shaft 136. Shaft 136 can be configured such that it can move a predetermined axial distance before engaging with the surface that forces rotation of shaft 136. In some embodiments, retainer 120 can be rotated about 90 degrees before disengaging from the medical device. One or more features of retainer 120 and/or shaft 136 can be used or adapted for use with any of the other retainers, retainer systems, shafts, and/or delivery catheters described herein.

Figure 8A:
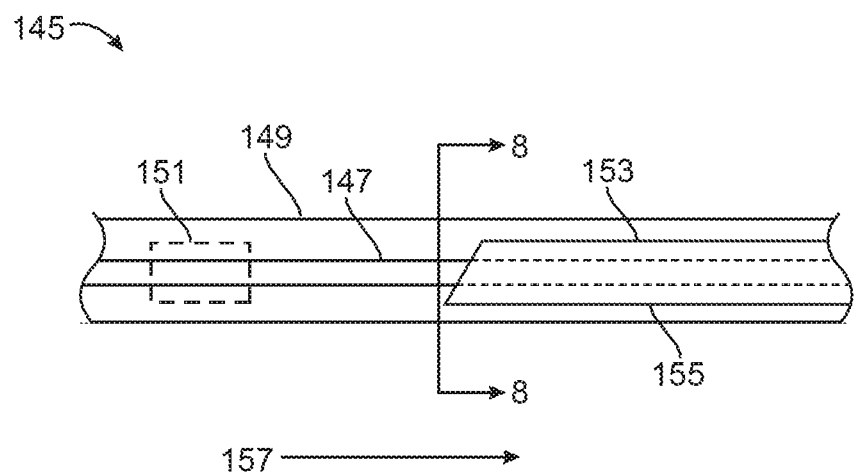
FIG. 8A illustrates a partially sectional view of a shaft system in accordance with an embodiment.
Figure 8B:
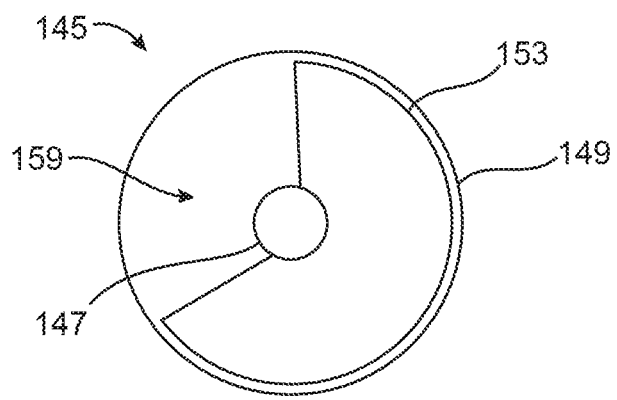
FIG. 8B illustrates a view of the shaft system of FIG. 8A along line 8-8 of FIG. 8A.

FIGS. 8A-B illustrate a shaft system 145 in accordance with an embodiment. In some embodiments, shaft system 145 can translate axial movement of a shaft into rotational movement of the shaft. In some embodiments, shaft system 145 can be included in one or more of the retainer systems described herein or in another suitable retainer system. In some embodiments, shaft system 145 can serve to allow one or more protrusions to "knock" or "bump" off a medical device from a retainer. FIG. 8A illustrates a partially sectional view of shaft system 145 and FIG. 8B illustrates a view of shaft system 145 along line 8-8 of FIG. 8A.

Shaft system 145 can include an inner shaft 147 disposed within an outer shaft 149. A protrusion 151 can be fixed to inner shaft 147. A guide 153 can be slidably disposed on inner shaft 147. Guide 153 can include an angled surface 155 configured to rotate protrusion 151 (which in some configurations can thereby rotate inner shaft 147) as protrusion 151 is moved in axial direction 157 against angled surface 155. In some embodiments, guide 153 includes a gap 159 which can allow protrusion 151 to slide within gap 159 once a desired rotation has been achieved. In some embodiments, gap 159 can extend along an entire length of guide 153. In some embodiments, gap 159 extends only along a portion of the length of guide 153.

Figure 9:
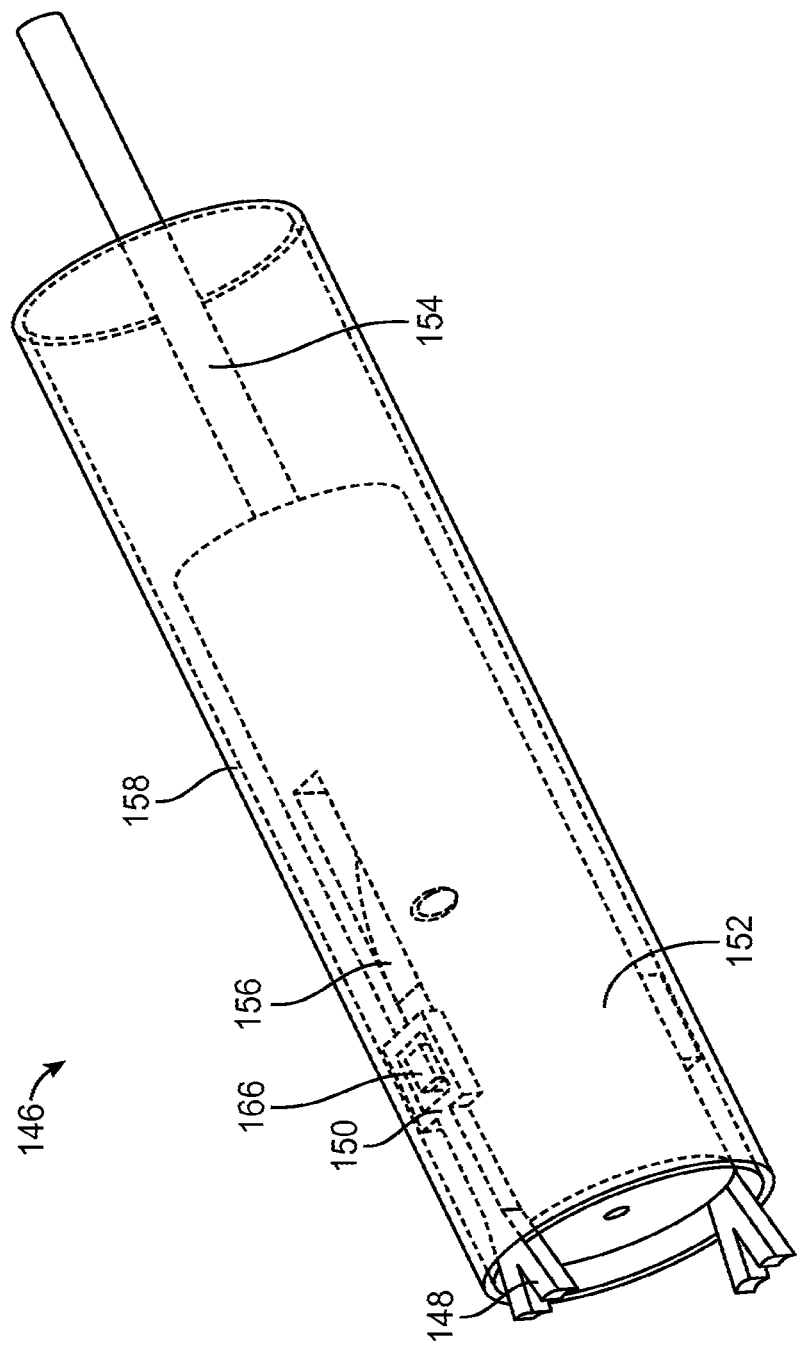
FIG. 9 illustrates a front-perspective view of a retainer system in accordance with an embodiment along with a portion of a medical device.
Figure 10A:
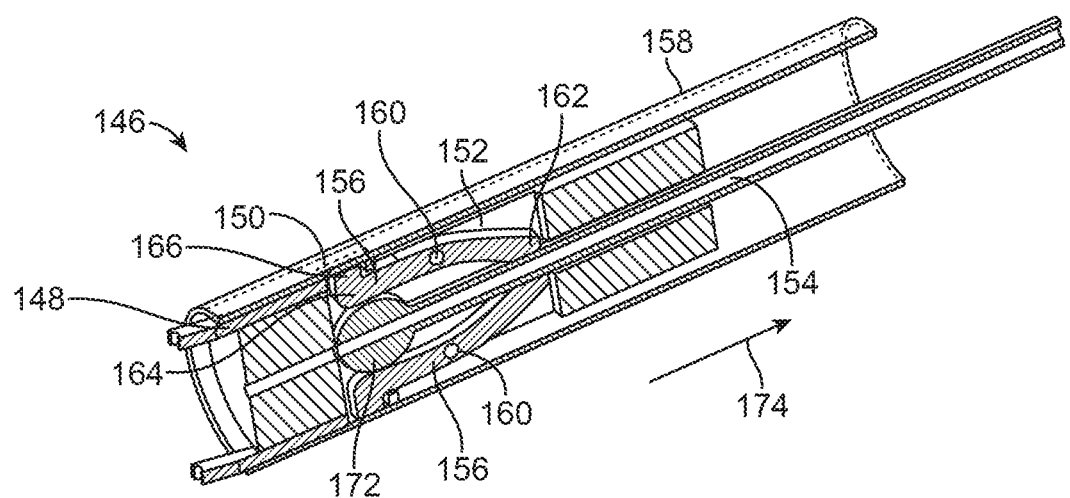
FIG. 10A illustrates a cross-sectional view of the retainer system of FIG. 9 at a first stage in a delivery operation.
Figure 10B:
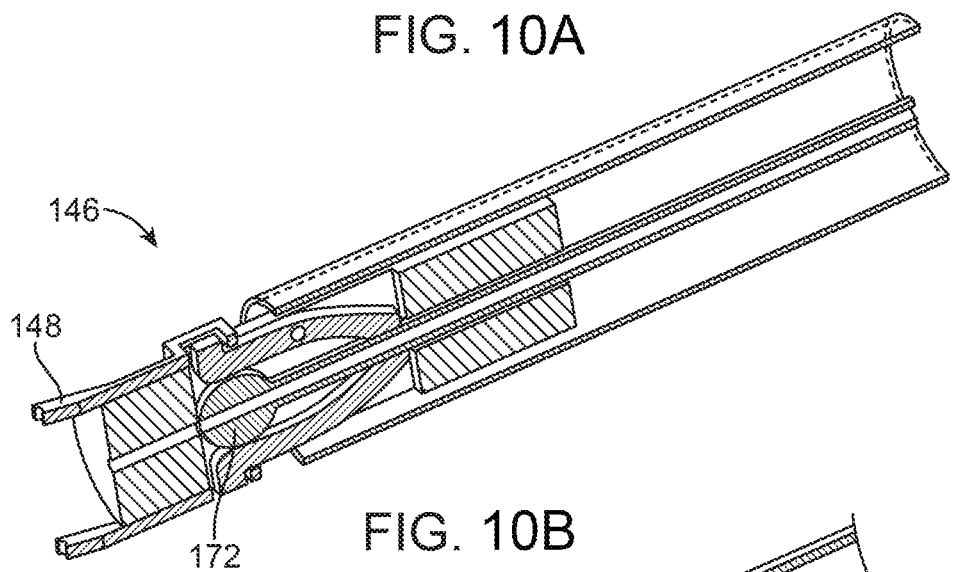
FIG. 10B illustrates a cross-sectional view of the retainer system of FIG. 9 at a second stage in a delivery operation.
Figure 10C:
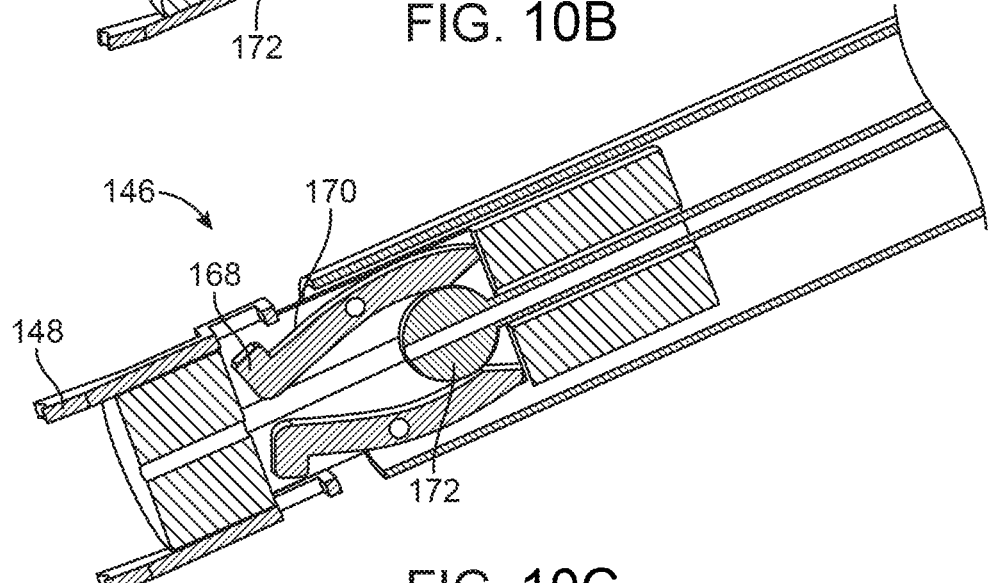
FIG. 10C illustrates a cross-sectional view of the retainer system of FIG. 9 at a third stage in a delivery operation.

FIGS. 9 and 10A-C illustrate a retainer system 146 and a portion of a medical device 148. FIG. 9 illustrates a front-perspective view of retainer system 146 engaged with eyelets 150 of medical device 148. FIGS. 10A-C illustrate various cross-sectional views of retainer system 146. Like several of the retainer systems described herein, retainer system 146 can be configured to both retain and controllably release a portion of a medical device.

Retainer system 146 can include base 152, actuator 154, and sheath 158. Retainer system 146 can include one or more retainers 156. One or more retainers 156 are connected to base 152 via a hinge 160 about which retainers 156 can rotate. Retainers 156 can be configured to release eyelets 150 by being retracted into base 152. Retainers 156 include a first end 162 on a proximal end of retainer 156 and a second end 164 on a distal end of retainer 156. Second end 164 includes a protrusion 166 which engages with a portion of medical device 148, such as eyelet 150. Stepped surfaces 168 and 170 of protrusion 166 are configured to engage with eyelets 150, in order to restrain movement of medical device 148 in one or both axial directions.

Actuator 154 includes a rounded protrusion 172 configured to engage with retainer 156 such that when rounded protrusion 172 is moved in proximal axial direction 174, protrusion 172 engages with first end 162 of retainer 156. Force from this engagement can cause first end 162 to move radially outward, which can rotate retainer 156 relative to hinge 160 to radially retract second end 164. Retraction of protrusion 166 on second end 164 allows eyelet 150 to disengage from retainer 156.

In operation, as shown in FIG. 10A, sheath 158 can initially cover base 152, retainer 156, actuator 154, and eyelets 150. Next, as shown in FIG. 10B, sheath 158 is retracted in axial direction 174 to expose eyelets 150. Next, as shown in FIG. 10C, actuator 154 is moved in axial direction 174, as protrusion 166 is pushed against first end 162, first end 162 is rotated radially outward, which forces second end 164 (as well as protrusion 166 on second end 164) to retract. As protrusion 166 retracts, eyelet 150 disengages from retainer 156 and is substantially free to move in one or both axial directions relative to retainer system 146. One or more features of retainer 156 and/or retainer system 146 can be used or adapted for use with any of the other retainers, retainer systems, and/or delivery catheters described herein.

Figure 11A:
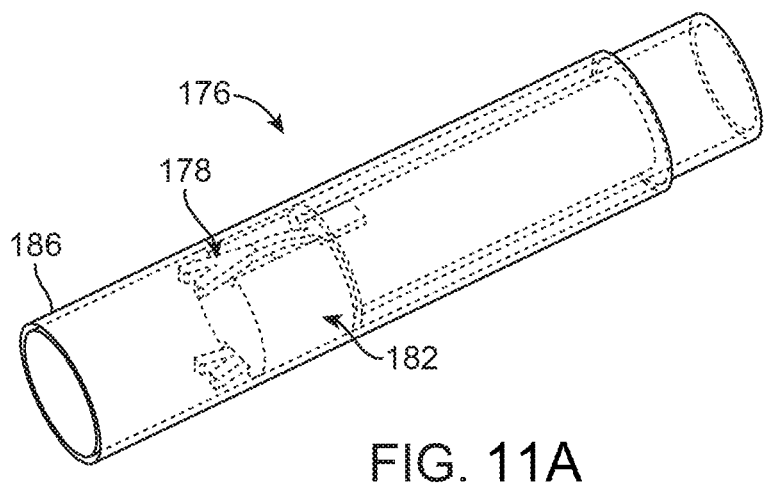
FIG. 11A illustrates a front perspective view of a retainer system in accordance with an embodiment along with a portion of a medical device at a first stage in a delivery operation.
Figure 11B:
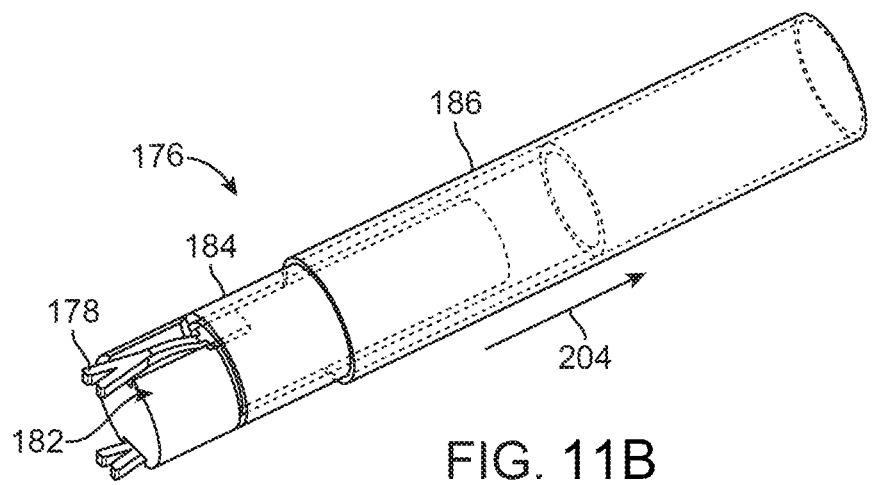
FIG. 11B illustrates a front perspective view of the retainer system of FIG. 11A at a second stage in a delivery operation.
Figure 11C:
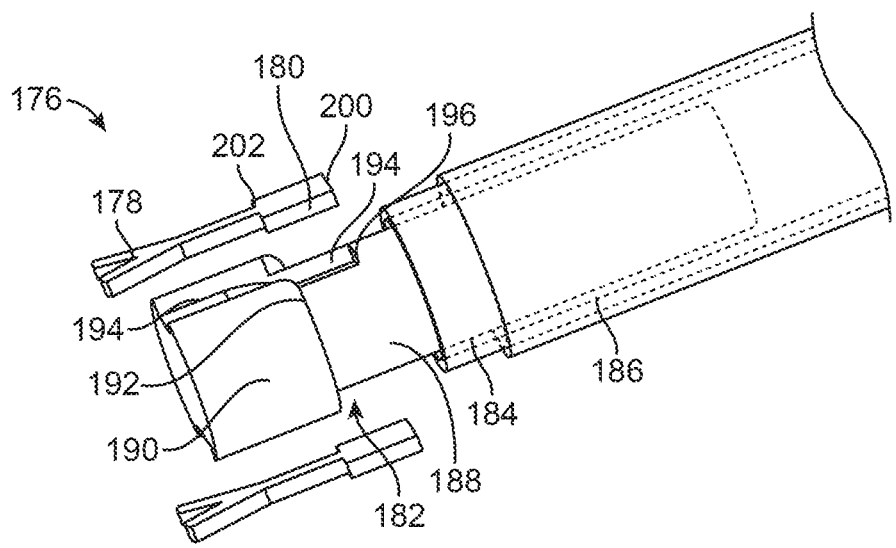
FIG. 11C illustrates a front perspective view of the retainer system of FIG. 11A at a third stage in a delivery operation.

FIGS. 11A-C illustrate retainer system 176 with a portion of a medical device 178. Like several of the retainer systems described herein, retainer system 176 can be configured to both retain and controllably release a medical device, such as a coupling portion 180 of medical device 178. Retainer system 176 can include a retainer 182 disposed within a lumen of an inner sheath 184. Inner sheath 184 itself can be disposed within a lumen of an outer sheath 186. In some embodiments, outer sheath 186 can cover the entirety of the remaining pieces of retainer system 176 (or one or more portions thereof) and/or the entirety of medical device 178 (or a portion thereof). Retainer 182 can be substantially cylindrical in shape with a reduced diameter portion 188, an enlarged diameter portion 190 and a stepped surface 192 separating the two portions. One or both of the reduced diameter portion 188 and enlarged diameter portion 190 can extend around an entire peripheral surface of retainer 182. In some embodiments, one or both of the reduced diameter portion 188 and enlarged diameter portion 190 do not extend around the entire peripheral surface of retainer 182. A recess 194 can be formed within both enlarged diameter portion 190 and reduced diameter portion 188. Recess 194 can be configured to receive a portion of medical device 178. Recess 194 includes stepped surfaces 196, which can be configured to engage with corresponding stepped surface 200 on coupling portion 180 in order to restrain movement of medical device 178 in an axial direction. Stepped surface 202 of coupling portion can engage with corresponding stepped surface 192 of enlarged diameter portion 190 in order to restrain movement of medical device 178 in an axial direction.

To disengage medical device 178 from retainer system 176, an operator can first retract outer sheath 186 in axial direction 204, which, as shown in FIG. 11B, can expose a portion of medical device 178 as well as retainer 182. The operator can then retract inner sheath 184 which, as shown in FIG. 11C, can fully expose medical device 178, including coupling portion 180. This can allow for medical device 178 to expand and disengage from retainer system 176. In some embodiments, inner sheath 184 and outer sheath 186 can be retracted at the same time. In some embodiments, inner sheath 184 can be retracted before outer sheath 186 is retracted. One or more features of retainer 182 and/or retainer system 176 can be used or adapted for use with any of the other retainers, retainer systems, and/or delivery catheters described herein.

Figure 12A:
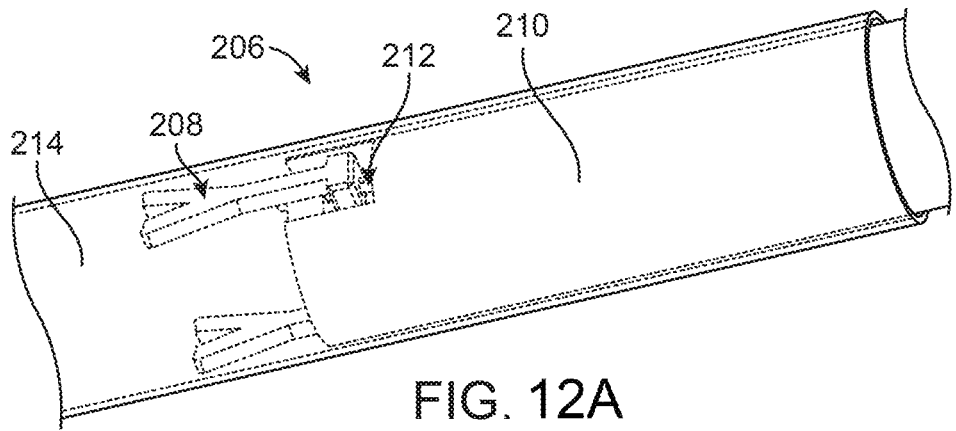
FIG. 12A illustrates a front perspective view of a retainer system in accordance with an embodiment along with a portion of a medical device at a first stage in a delivery operation.
Figure 12B:
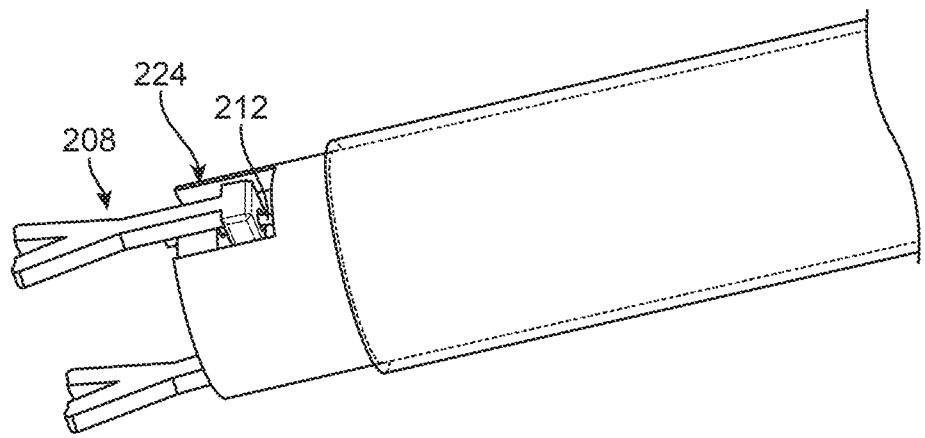
FIG. 12B illustrates a front perspective view of the retainer system of FIG. 12A at a second stage in a delivery operation.
Figure 12C:
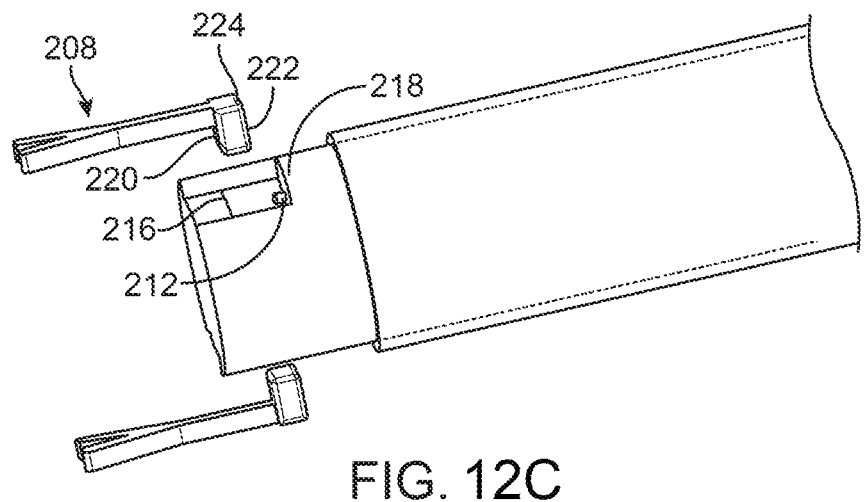
FIG. 12C illustrates a front perspective view of the retainer system of FIG. 12A at a third stage in a delivery operation.

FIGS. 12A-C illustrate a retainer system 206 and a portion of a medical device 208. Like several of the retainer systems described herein, retainer system 206 can be configured to both retain and controllably release a portion of a medical device, such as medical device 208. Retainer system 206 can include a base 210, one or more pins 212 configured to retract into base 210, and a sheath 214. In some embodiments, sheath 214 can cover the entirety of the other pieces of retainer system 206 (or one or more portions thereof) and/or the entirety of medical device 208 (or a portion thereof). Stepped surfaces 216 and 218 of base 210 are configured to engage with corresponding stepped surfaces 220 and 222 on coupling portion 224 of medical device 208 and can restrain movement of medical device 208 in one or both axial directions.

To disengage medical device 208 from retainer system 206, an operator can first retract sheath 214 which, as shown in FIG. 12B, can fully expose coupling portion 224 of medical device 208. The operator can then retract pins 212 from coupling portion 224. This can allow for medical device 208 to expand and disengage from retainer system 206. In some embodiments, sheath 214 and pins 212 can be retracted at the same time. In some embodiments, pins 212 can be retracted before sheath 214 is retracted. One or more features of retainer system 206 can be used or adapted for use with any of the other retainers, retainer systems, and/or delivery catheters described herein.

Figure 13C:
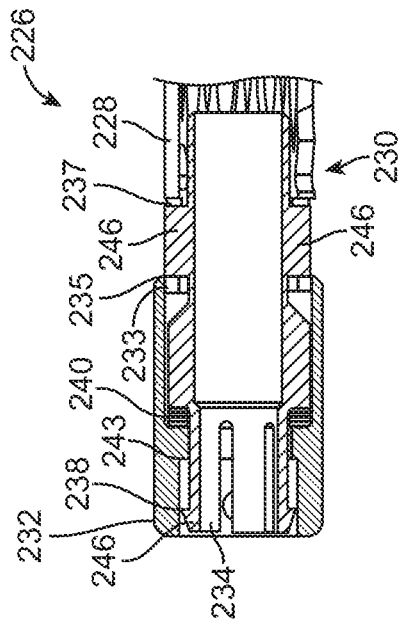
FIG. 13C illustrates a cross-sectional view of the retainer system of FIG. 13A at a first stage.
Figure 13D:
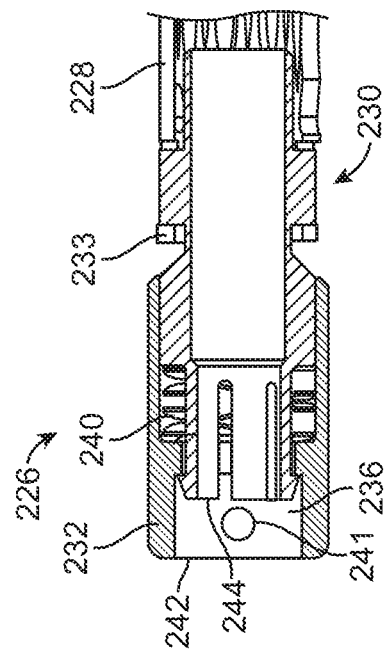
FIG. 13D illustrates a cross-sectional view of the retainer system of FIG. 13A at a second stage in a delivery operation.
Figure 13A:
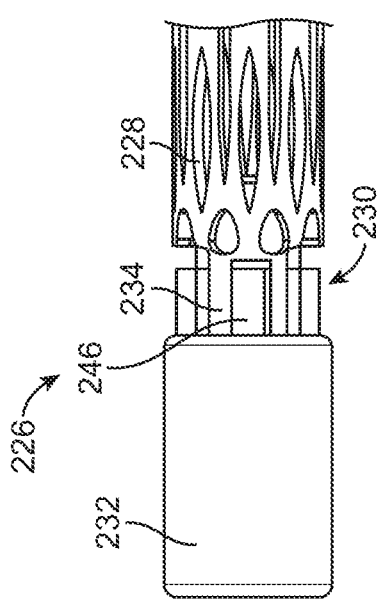
FIG. 13A illustrates a front view of a retainer system in accordance with an embodiment along with a portion of a medical device at a first stage in a delivery operation.
Figure 13B:
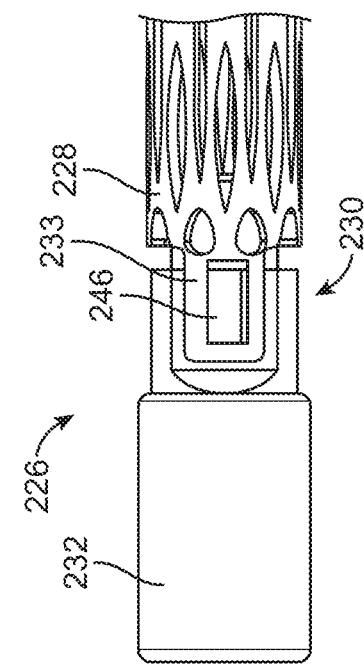
FIG. 13B illustrates a front view of the retainer system of FIG. 13A at a second stage in a delivery operation.

FIGS. 13A-D illustrate a retainer system 226 and a portion of a medical device 228. FIGS. 13A-B respectively illustrate front views of retainer system 226 in a closed state and an open state. FIGS. 13C-D respectively illustrate cross-sectional views of retainer system 226 in a closed state and an open state. Retainer system 226 as shown in FIGS. 13C-D is rotated 90 degrees about its axis relative to retainer system 226 as shown in FIGS. 13A-B. Like certain retainer systems described herein, retainer system 226 can be configured to both retain and controllably release a portion of a medical device, such as medical device 228. Retainer system 226 can include a base 230 and a cap 232 configured to cover a portion of medical device 228, such as eyelets 233. In some embodiments, cap 232 can cover the entirety of the other parts of retainer system 226 (or one or more portions thereof) and/or the entirety of medical device 228 (or a portion thereof). For example, as shown in FIGS. 13A and 13C, when in a fully closed state, cap 232 can cover only a portion of eyelets 233.

Stepped surfaces 235 and 237 of a protrusion 246 formed on base 230 are configured to engage with eyelet 233 in order to restrain movement of medical device 228 in one or both axial directions. Retainer system 226 can include a spring 240 that spring-loads cap 232, which in some embodiments can facilitate more reliable movement of cap 232 and more reliable disengagement of medical device 228 from retainer system 226. In some embodiments, base 230 includes extensions 234 which extend into a cavity 236 formed in cap 232. Extensions 234 can include a protrusion 239 having a stepped surface 238 configured to engage with a corresponding stepped surface 243 of cap 232. In some embodiments, such as the embodiment shown in FIG. 13D, such a configuration can restrain movement of cap 232 in one or both axial directions. In some embodiments, cap 232 can include an aperture 241 formed therein. In some embodiments, aperture 241 can serve as an air vent for cap 232. In some embodiments, an inside surface 242 of cap 232 can abut an end 244 of extensions 234 when retainer system 226 is in a closed state. In some embodiments, such a configuration can restrain movement of cap 232 in an axial direction.

To disengage medical device 228 from retainer system 226, an operator can actuate cap 232 to retract it from covering eyelets 233. As shown in FIGS. 13B and 13D, this retraction can fully expose eyelets 233, which can allow medical device 228 to expand and disengage from retainer system 226. One or more features of retainer system 226 can be used or adapted for use with any of the other retainers, retainer systems, and/or delivery catheters described herein.

Figure 14:
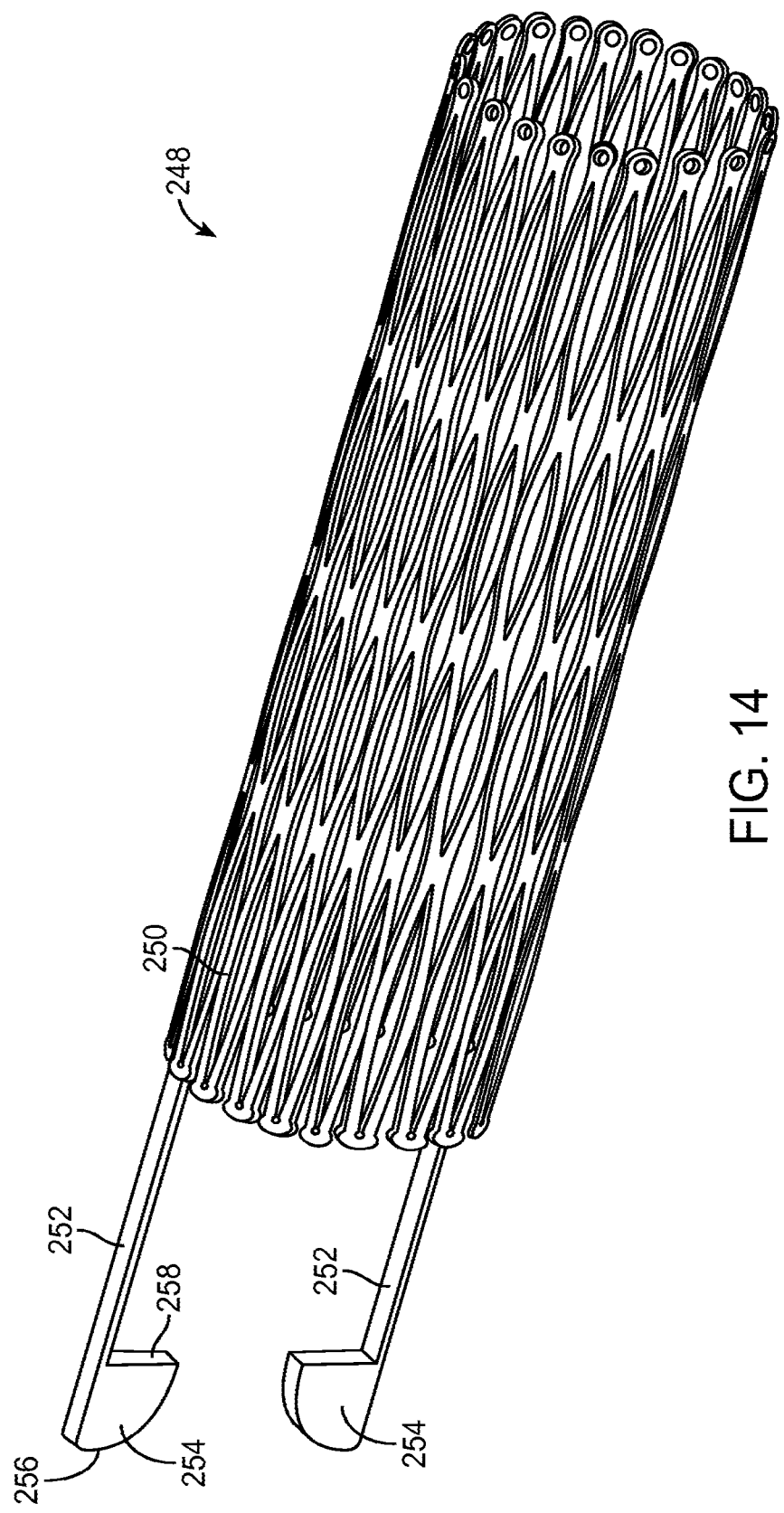
FIG. 14 illustrates a medical device for use with one or more of the medical device delivery systems described herein.

FIG. 14 illustrates a medical device 248 that can be used with one or more retainer systems described herein. Medical device 248 can include a frame 250 with one or more arms 252 extending therefrom. To facilitate disengagement from a retainer system (not shown), one or more of the arms 252 can include coupling portions 254 having a curved surface 256 on a first side and a stepped surface 258 on a second side. A stepped surface of the retainer system can be configured to engage with stepped surface 258 on coupling portion 254 in order to restrain movement of medical device 248 in one or both axial directions. In some embodiments, curved surface 256 can facilitate disengagement of medical device 248 from a retainer system in one or more ways. For example, in some embodiments, curved surface 256 can reduce torque and/or friction generated between medical device 248 and a portion of a retainer system. In some embodiments, curved surface 256 can be configured to re-direct axial force of coupling portion 254 into outward radial force to facilitate disengagement from the retainer system. One or more features of medical device 248 can be used or adapted for use with any of the other retainers, retainer systems, and/or delivery catheters described herein.

FIGS. 15A-B illustrate medical device 248 within a portion of a delivery catheter 260 in accordance with an embodiment. FIG. 15A illustrates a partially transparent front view of delivery catheter 260. FIG. 15B illustrates a cross-sectional view of delivery catheter 260. Delivery catheter 260 can include a medical device 248 and a tip 262 connected via a shaft 264 to a retainer system 266. Retainer system 266 can include a retainer 268, and a sheath 270 (shown in FIG. 15A). In some embodiments, sheath 270 can cover the entirety of the other pieces of retainer system 266 (or one or more portions thereof) and/or the entirety of medical device 248 (or a portion thereof). Stepped surface 272 of retainer 268 is configured to engage with corresponding stepped surface 258 on coupling portion 254 of medical device 248 in order to restrain movement of medical device 248 in one or both axial directions. Curved surface 274 of retainer 268 is configured to engage with corresponding curved surface 256 of coupling portion 254, which can facilitate disengagement of medical device 248 from retainer system 266. One or more features of retainer 268, retainer system 266, and/or delivery catheter 260 can be used or adapted for use with any of other retainers, retainer systems, and/or delivery catheters described herein.

FIGS. 16A-C illustrate medical device 248 within a portion of a delivery catheter 278 in accordance with an embodiment. Delivery catheter 278 can include medical device 248 and a tip 280 connected via a shaft 282 to a retainer system 284. Retainer system 284 can include a retainer 286, and a sheath 288. FIG. 16A illustrates a partially transparent front view of a portion of delivery catheter 278. FIG. 16B illustrates a cross-sectional view of a portion of delivery catheter 278 with sheath 288 covering retainer system 284. FIG. 16C illustrates a cross-sectional view of a portion of delivery catheter 278 with sheath 288 retracted to expose coupling portion 254 of medical device 248.

Retainer system 284 can include a retainer 286 and a sheath 288. In some embodiments, sheath 288 can cover the entirety of the other pieces of retainer system 284 (or one or more portions thereof) and/or the entirety of medical device 248 (or a portion thereof). Stepped surface 290 of retainer 286 is configured to engage with corresponding stepped surface 258 on coupling portion 254 of medical device 248 in order to restrain movement of medical device 248 in one or both axial directions. Curved surface 292 of retainer 286 is configured to engage with corresponding curved surface 256 of coupling portion 254, which can facilitate disengagement of medical device 248 from retainer system 284. One or more features of retainer 286, retainer system 284, and/or delivery catheter 278 can be used or adapted for use with any of other retainers, retainer systems, and/or delivery catheters described herein.

The choice of materials for the various valve prostheses described herein can be informed by the requirements of mechanical properties, temperature sensitivity, biocompatibility, moldability properties, or other factors apparent to a person having ordinary skill in the art. For example, one more of the parts (or a portion of one of the parts) can be made from suitable plastics, such as a suitable thermoplastic, suitable metals, and/or other suitable materials.

The foregoing description of the invention has been presented for purposes of illustration and description. It is not intended to be exhaustive or to limit the invention to the precise form disclosed. Other modifications and variations can be possible in light of the above teachings. The embodiments and examples were chosen and described in order to best explain the principles of the invention and its practical application and to thereby enable others skilled in the art to best utilize the invention in various embodiments with modifications as are suited to the particular use contemplated. It is intended that the appended claims be construed to include other alternative embodiments of the invention.

The invention claimed is:

1. A medical device delivery system comprising:
a catheter;
a retainer disposed within the catheter and including a first end and a second end; and
an actuator, the actuator comprising a shaft with a protrusion at a distal portion thereof,
wherein the actuator includes a first actuator position wherein the protrusion engages the second end of the retainer thereby causing the second end of the retainer to move radially outward such that the second end of the retainer is engaged with a medical device to restrain axial movement of the medical device and a second actuator position wherein the protrusion engages the first end of the retainer, thereby causing the retainer to rotate about a hinge causing the second end of the retainer to move radially inward such that the second end of the retainer is disengaged from the second end from the medical device.

2. The medical device delivery system of claim 1, further comprising:
a base attached to the retainer via the hinge.

3. The delivery system of claim 1, further comprising:
an inflatable balloon configured to facilitate disengagement of the medical device from the retainer by providing a radially outward force on a portion of the medical device when the balloon is inflated.

4. The delivery system of claim 1, wherein the first actuator position is a distal position and proximal retraction of the shaft retracts the protrusion proximally such that the protrusion engages the first end of the retainer.

5. The delivery system of claim 1, wherein the catheter comprises an outer sheath, wherein the retainer is disposed within the outer sheath, wherein the outer sheath is slidable relative to the retainer and includes a first sheath position wherein the outer sheath covers the second end of the retainer and a second sheath position wherein the outer sheath does not cover the second end of the retainer.

6. The delivery system of claim 1, wherein the retainer comprises two retainer arms, each having a first end a second end, wherein the second end of each retainer arm is engaged with the medical device, and each retainer arm being attached to a base via a hinge,
wherein when the actuator engages the first end of each retainer arm, each retainer arm rotates about the hinge to disengage the second end of each retainer arm from the medical device.

7. The delivery system of claim 1, wherein the second end of the retainer includes a retainer protrusion extending radially outwardly to engage the medical device when the actuator is in the first actuator position.

8. A medical device delivery system comprising:
a catheter;
a retainer disposed within the catheter and engaged with the medical device to restrain relative movement of the medical device in an axial direction, wherein the retainer comprises two retainer arms, each having a first end a second end, wherein the second end of each retainer arm is engaged with the medical device, and each retainer arm being attached to a base via a hinge; and
an actuator configured to radially retract the retainer and disengage the medical device from the retainer, wherein the actuator comprises a shaft with a protrusion at a distal portion thereof,
wherein the protrusion is disposed between the two retainer arms,
wherein when the protrusion is disposed between the retainer arms at the second ends of the retainer arms, the second ends of the retainer arms are engaged with the medical device, and
wherein retraction of the shaft retracts the protrusion such that the protrusion engages the first end of each of the retainer arms causing each retainer arm to rotate about the hinge to disengage the second end of each retainer arm from the medical device.

9. The delivery system of claim 8, wherein the catheter comprises an outer sheath, wherein the retainer is disposed within the outer sheath, wherein the outer sheath is slidable relative to the retainer and includes a first position wherein the outer sheath covers the second end each retainer arm and a second position wherein the outer sheath does not cover the second end of each retainer arm.

10. The delivery system of claim 8, wherein the second end of each retainer arm includes a retainer protrusion extending radially outwardly to engage the medical device when the protrusion of the actuator is disposed between the second ends of the retainer arms.

* * * * *